(12) United States Patent
Kim (10) Patent No.: US 12,347,565 B2
(45) Date of Patent: Jul. 1, 2025

(54) APPARATUS AND METHOD OF PROVIDING SERVICE ACCORDING TO STATUS OF PASSENGER IN AIRCRAFT DURING AUTONOMOUS FLIGHT

(71) Applicants: HYUNDAI MOTOR COMPANY, Seoul (KR); KIA CORPORATION, Seoul (KR)

(72) Inventor: Kye Yoon Kim, Gyeonggi-do (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 132 days.

(21) Appl. No.: 18/138,897

(22) Filed: Apr. 25, 2023

(65) Prior Publication Data
US 2024/0190570 A1   Jun. 13, 2024

(30) Foreign Application Priority Data

Dec. 12, 2022  (KR) .................. 10-2022-0172998

(51) Int. Cl.
   *G08G 5/00*     (2025.01)
   *G05D 1/00*     (2006.01)
   (Continued)

(52) U.S. Cl.
   CPC .......... *G16H 50/30* (2018.01); *G05D 1/0676* (2013.01); *G05D 1/101* (2013.01); *G06V 10/00* (2022.01);
   (Continued)

(58) Field of Classification Search
   CPC ........ G16H 50/30; G16H 50/20; G16H 40/63; G06V 20/59; G06V 40/174; G06V 10/00;
   (Continued)

(56) References Cited

U.S. PATENT DOCUMENTS

| | | | |
|---|---|---|---|
| 9,310,222 B1 | 4/2016 | Suiter et al. | |
| 2006/0025900 A1* | 2/2006 | Arnouse | B64D 45/0034 701/3 |
| 2012/0132746 A1* | 5/2012 | Sizelove | A47C 7/624 345/157 |
| 2013/0338857 A1 | 12/2013 | Sampigethaya | |

(Continued)

FOREIGN PATENT DOCUMENTS

| | | |
|---|---|---|
| DE | 10 2019 204954 A1 | 10/2020 |
| EP | 3267424 A1 | 1/2018 |

(Continued)

OTHER PUBLICATIONS

Extended European Search Report dated Mar. 14, 2024 issued in European Patent Application No. 23197123.5.

*Primary Examiner* — Abdul-Samad A Adediran
(74) *Attorney, Agent, or Firm* — Morgan, Lewis & Bockius LLP (57) ABSTRACT

A service providing apparatus of providing a service according to a state of a passenger in aircraft during autonomous flight includes a processor; and a storage medium recording one or more programs configured to be executable by the processor, wherein the one or more programs include instructions for an input/output (I/O) module receiving biometric data and a captured image of a passenger in real time, a determination module determining a state of the passenger based on the biometric data and the captured image of a passenger, and a control module performing a preset process according to the state of the passenger, wherein the preset process includes: a first process for adjusting a flight path of the aircraft when the state of the passenger is an emergency state or a second process for relieving tension when the state of the passenger is a state of tension.

16 Claims, 6 Drawing Sheets

(51) Int. Cl.
*G06V 10/00* (2022.01)
*G06V 10/764* (2022.01)
*G06V 20/59* (2022.01)
*G06V 40/16* (2022.01)
*G16H 50/20* (2018.01)
*G16H 50/30* (2018.01)

(52) U.S. Cl.
CPC ............ *G06V 10/764* (2022.01); *G06V 20/59* (2022.01); *G06V 40/174* (2022.01); *G16H 50/20* (2018.01)

(58) Field of Classification Search
CPC .... G06V 10/764; G05D 1/0676; G05D 1/101; A61B 5/02055; B64D 45/0034; H04N 21/41422; A47C 7/624
USPC ............................................. 345/157; 701/3
See application file for complete search history.

(56) References Cited

U.S. PATENT DOCUMENTS

| | | |
|---|---|---|
| 2014/0003659 A1 | 1/2014 | Hoffmann et al. |
| 2015/0287187 A1 | 10/2015 | Redtel |
| 2018/0374368 A1* | 12/2018 | Bolling .................. G16H 40/63 |
| 2019/0266472 A1 | 8/2019 | Johnson |
| 2019/0391581 A1* | 12/2019 | Vardaro ............. A61B 5/02055 |
| 2020/0026309 A1 | 1/2020 | Ma |
| 2020/0128383 A1 | 4/2020 | Maier et al. |
| 2022/0306143 A1 | 9/2022 | Samani et al. |
| 2022/0382799 A1* | 12/2022 | Chen ................ H04N 21/41422 |

FOREIGN PATENT DOCUMENTS

| | | |
|---|---|---|
| KR | 10-2006-0022935 A | 3/2006 |
| KR | 10-2020-0072581 A | 6/2020 |
| KR | 10-2021-0096431 A | 8/2021 |
| KR | 10-2303416 B1 | 9/2021 |
| WO | 2017/197208 A1 | 11/2017 |
| WO | 2019/125222 A1 | 6/2019 |

* cited by examiner

APPARATUS AND METHOD OF PROVIDING SERVICE ACCORDING TO STATUS OF PASSENGER IN AIRCRAFT DURING AUTONOMOUS FLIGHT

CROSS-REFERENCE TO RELATED APPLICATION (S)

This application claims the benefit under 35 USC 119 (a) of Korean Patent Application No. 10-2022-0172998 filed on Dec. 12, 2022 in the Korean Intellectual Property Office, the entire disclosure of which is incorporated herein by reference for all purposes.

TECHNICAL FIELD

The present disclosure relates to an apparatus and method of providing a service according to a state of a passenger in an aircraft during an autonomous flight.

BACKGROUND

Recently, research and development of aircraft capable of autonomous flight has steadily progressed, and by using such aircraft, passengers may be transported to a desired destination.

However, in the case of an aircraft without an in-flight crew, there is a problem in that it may be difficult to provide a prompt service when a passenger complains of tension or an emergency occurs during autonomous flight.

SUMMARY

Exemplary embodiments provide an apparatus and method for providing a service according to a state of a passenger in an aircraft during an autonomous flight, capable of promptly providing a service for a passenger in a nervous or emergency state.

According to an exemplary embodiment, a service providing apparatus of providing a service according to a state of a passenger in aircraft during autonomous flight includes: a processor; and a storage medium recording one or more programs configured to be executable by the processor, wherein the one or more programs include instructions for an input/output (I/O) module receiving biometric data and a captured image of a passenger in real time; a determination module determining a state of the passenger based on the biometric data and the captured image of a passenger; and a control module performing a preset process according to the state of the passenger, wherein the preset process includes: a first process for adjusting a flight path of the aircraft when the state of the passenger is an emergency state or a second process for relieving tension when the state of the passenger is a state of tension.

According to another exemplary embodiment, a method of providing a service according to a state of a passenger in aircraft during autonomous flight includes: a first operation in which an input/output (I/O) module receives biometric data and a captured image of a passenger in real time; a second operation in which a determination module determines a state of the passenger based on the biometric data and the captured image of a passenger; and a third operation in which a control module performs a preset process according to the state of the passenger, wherein the preset process includes: a first process for adjusting a flight path of the aircraft when the state of the passenger is an emergency state or a second process for relieving tension when the state of the passenger is a state of tension.

BRIEF DESCRIPTION OF DRAWINGS

The above and other aspects, features, and advantages of the present inventive concept will be more clearly understood from the following detailed description, taken in conjunction with the accompanying drawings, in which.

DETAILED DESCRIPTION

Hereinafter, exemplary embodiments in the present disclosure will be described with reference to the accompanying drawings. However, the exemplary embodiments of the present disclosure may be modified in various other forms, and the scope of the present disclosure is not limited only to the exemplary embodiments described below. The shapes and sizes of elements in the drawings may be exaggerated for clarity, and elements indicated by the same reference numerals in the drawings are the same elements.

Figure 1:
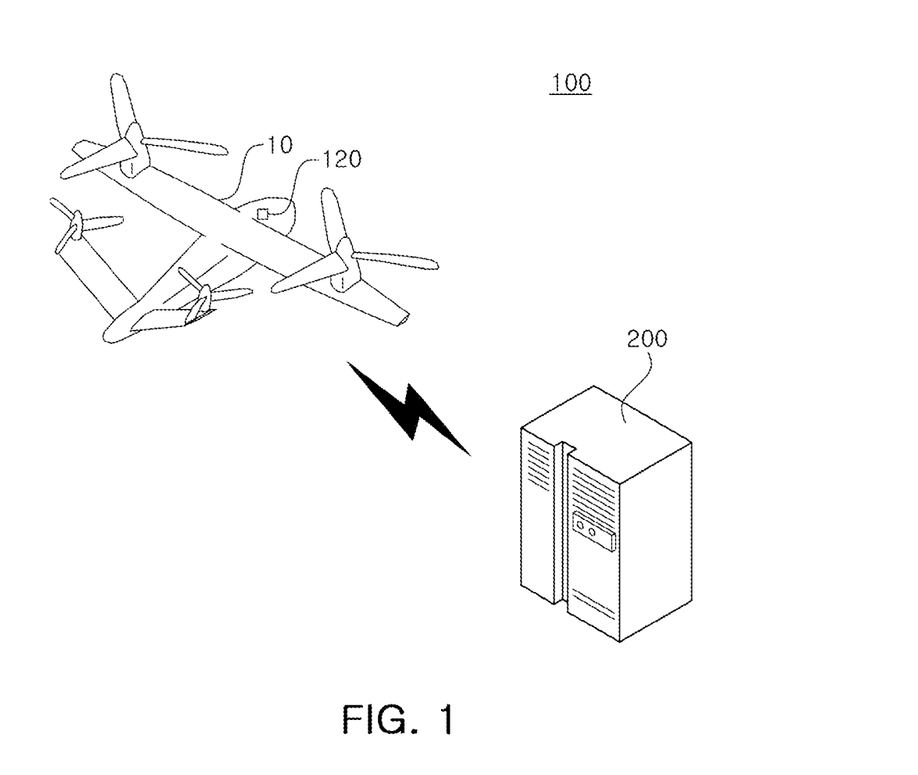
FIG. 1 is a configuration diagram of an entire system including an aircraft and a control device according to an exemplary embodiment in the present disclosure.

FIG. 1 is a configuration diagram of an entire system including an aircraft and a control device according to an exemplary embodiment in the present disclosure. Also, FIG. 2 is an internal block diagram of a service providing apparatus and a control device mounted on an aircraft according to an exemplary embodiment in the present disclosure.

Figure 2:
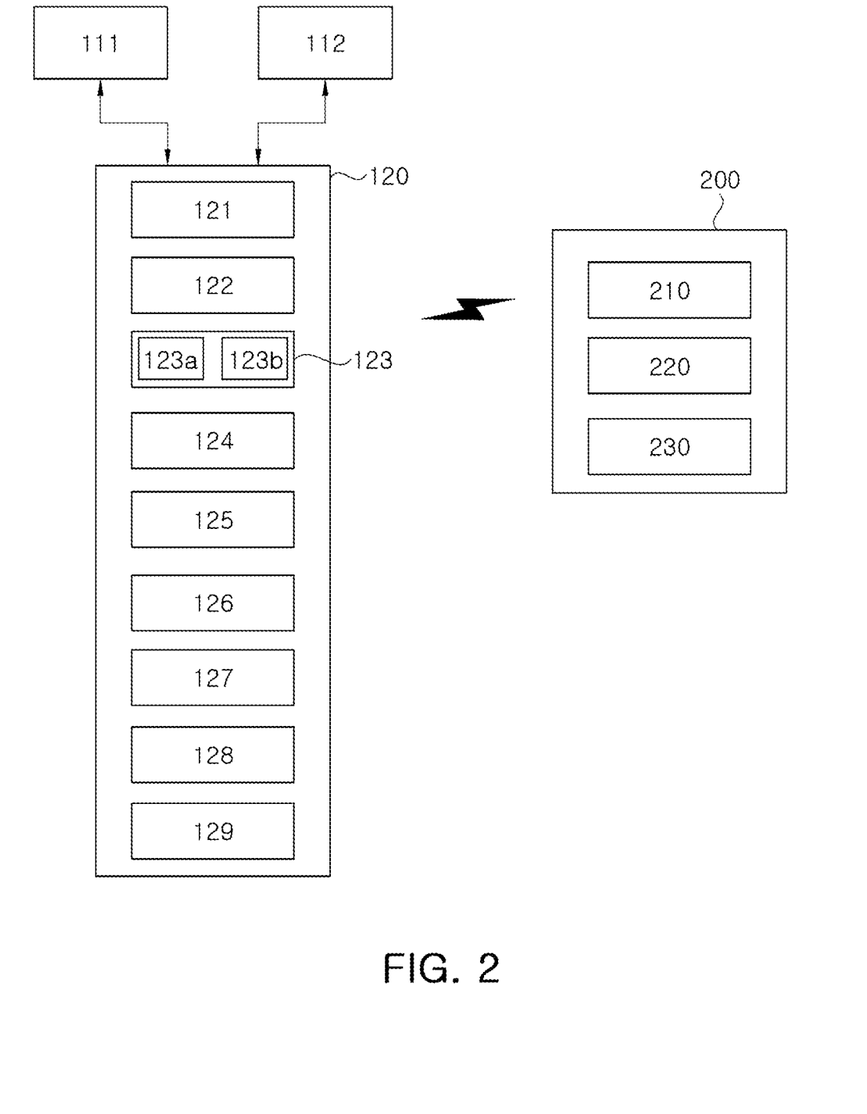
FIG. 2 is an internal block diagram of a service providing apparatus and a control device mounted on an aircraft according to an exemplary embodiment in the present disclosure.

Referring to FIGS. 1 to 2, an overall system 100 may include an aircraft 10 and a control device 200, and the aircraft 10 may include a service providing apparatus 120 according to an exemplary embodiment in the present disclosure. The aforementioned service providing apparatus 120 may include an input/output (I/O) module 121, a determination module 122, a machine learning model 123, a control module 124, a driving module 125, a global positioning system (GPS) module 126, and a convenience device 127, a storage module 128, and a communication module 129, and the machine learning model 123 may include a first machine learning model 123a and a second machine learning model 123b.

According to an exemplary embodiment of the present disclosure, the service providing apparatus 120 may include a processor (e.g., computer, microprocessor, CPU, ASIC, circuitry, logic circuits, etc.) and an associated non-transitory memory storing software instructions which, when executed by the processor, provides the functionalities of the input/output (I/O) module 121, the determination module 122, the machine learning model 123, the control module 124, the driving module 125, the global positioning system (GPS) module 126, the convenience device 127, the storage module 128, and the communication module 129. Herein, the memory and the processor may be implemented as separate semiconductor circuits. Alternatively, the memory and the processor may be implemented as a single integrated semiconductor circuit. The processor may embody one or more processor (s).

In the present disclosure, the aircraft 10 may refer to a mobility vehicle that may move by flying in the sky. That is, aircraft may include vehicles capable of flying on the ground with wheels separated from the ground, while moving on the ground using wheels, in addition to referring to helicopters, drones, fixed-wing airplanes, etc.

Also, the aircraft 10 may include manned aircraft and unmanned aerial vehicles. A manned aircraft may include a body capable of operating autonomously in addition to a body controlled by a pilot. In addition, in the present disclosure, a crew may not board the aircraft 10.

Meanwhile, the control device 200 may include a control module 210, a communication module 220, and a storage module 230.

According to an exemplary embodiment of the present disclosure, the control device 200 may include a processor (e.g., computer, microprocessor, CPU, ASIC, circuitry, logic circuits, etc.) and an associated non-transitory memory storing software instructions which, when executed by the processor, provides the functionalities of the control module 210 and the communication module 220. Herein, the memory and the processor may be implemented as separate semiconductor circuits. Alternatively, the memory and the processor may be implemented as a single integrated semiconductor circuit. The processor may embody one or more processor (s).

Hereinafter, the service providing apparatus 120 providing a service according to a state of a passenger in an aircraft during autonomous flight and the control device 200 according to an exemplary embodiment in the present disclosure will be described in detail with reference to FIGS. 1 and 2.

First, the I/O module 121 of the service providing apparatus 120 may receive biometric data and a captured image of a passenger in real time. The received biometric data and the captured image of a passenger may be transmitted to the determination module 122.

The biometric data of the passenger may include at least one of a heart rate, a sweat output, a grip strength, a blood pressure, a body temperature, and a respiration rate of the passenger, and the biometric data may be measured through the sensor module 111. The sensor module 111 may include a heart rate sensor for measuring a heart rate, a sweat sensor for measuring sweat output, a pressure sensor for measuring grip strength, and a blood pressure sensor for measuring blood pressure, a body temperature sensor for measuring a body temperature, a respiration rate sensor for measuring a respiration rate, and the like may be included. This sensor module 111 may be a wearable device worn by passengers.

In addition, the captured image is an image obtained by imaging the face and body parts (arms, legs, etc.) of the passenger sitting in the seat, and such captured image may be captured by the camera 112.

In addition, the I/O module 121 may relieve passengers' tension by providing a video or music for tension. In order to provide images or music, the I/O module 121 may include a touchscreen, a speaker device, a display device, a projector, headphones, and the like.

The determination module 122 of the service providing apparatus 120 may determine a state of the passenger based on the biometric data and the captured image. Here, the state of the passenger may be an emergency state or a state of tension.

Specifically, the determination module 122 may determine whether a state of the passenger is an emergency state based on a combination of classification result from the machine learning model 123 to which the captured image of a passenger is input and comparison result between at least one of a heart rate, a sweat output, a grip strength, a blood pressure, and a respiration rate of the passenger with each preset reference value. The aforementioned reference value may vary depending on the gender, age, etc. of the passenger, but is not limited to a specific value here.

Meanwhile, the machine learning model 123 described above may include a first machine learning model 123a for classifying a facial expression of the passenger in the captured image and a second machine learning model 123b for classifying a body posture of the passenger in the captured image.

The machine learning model 123 described above may be a model using a convolution neural network (CNN) as a representative example, but it should be appreciated that the machine learning model 123 may be any device without being thereto, as long as the device is able to classify the facial expression or body posture of the passenger.

Specifically, the first machine learning model 123a may classify the facial expression of the passenger as pain, fear, tension, disgust, stuffiness, discomfort, and others. Here, the others may include facial expressions other than pain, fear, tension, disgust, stuffiness, and discomfort.

In addition, the second machine learning model 123b may classify the body posture of the passenger as one of a posture with eyes closed, a posture with hands put on the head, a posture in which the face is lowered down forwardly and is not visible, and others. Here, the others may be body postures other than the posture with eyes closed, the posture with hands put on the head, and the posture in which the face is lowered down forwardly and is not visible.

Although the present disclosure described above specifically limits the facial expression and body posture of the passenger, this is to help understanding of the present disclosure, and it is obvious to those skilled in the art that various facial expressions and various body postures may be further included depending on the type of disease.

The type and classification result of biometric data used when determining such an emergency state may be different for each disease.

For example, when an emergency state is caused by a passenger's panic attack, various symptoms may appear. For example, a symptom of an increase in heart rate, a symptom of sweating, a symptom of an increase in body temperature, etc. may appear as biometric data, and the facial expression of a passenger during capturing an image may appear as an expression of pain, stuffiness, or discomfort.

In addition, when the emergency state is caused by a stroke of a passenger, the passenger's body posture in the captured image may appear as a symptom, such as the posture with hands put on the head due to a headache or a drooping arm, and a facial expression in the captured image may appear as an expression of discomfort.

Therefore, according to an exemplary embodiment in the present disclosure, whether the state of the passenger is an emergency state maybe be determined based on a combination of classification result from the machine learning model 123 to which the captured image of a passenger is input and comparison result between at least one of a heart rate, a sweat output, a grip strength, a blood pressure, and a respiration rate of the passenger with each preset reference value In addition, the determination module 122 may further estimate a disease based on the combination of classification result from the machine learning model 123 to which the captured image is input and comparison result between at least one of the heart rate, sweat output, grip strength, blood pressure, and respiration rate of the passenger with each preset reference value. However, when there are multiple estimated diseases, the determination module 122 may estimate a disease by considering a disease according to the underlying disease of the passenger or family history as a priority.

In addition, the determination module 122 may determine whether the state of the passenger is a state of tension based on a classification result from the first machine learning model 123*a* to which the captured image of a passenger is input or the comparison result between at least one of the heart rate, sweat output, grip strength, blood pressure, and respiration rate of the passenger with each preset reference value.

According to an exemplary embodiment in the present disclosure, based on the classification result from the first machine learning model 123*a* to which the captured image is input and the comparison result between at least one of the heart rate, sweat output, grip strength, blood pressure, and respiration rate of the passenger with each preset reference value, the determination module 122 may determine whether the passenger is in a state of tension.

Meanwhile, the control module 124 of the service providing apparatus 120 may perform a preset process according to the state of the passenger.

Here, the preset process may include a first process for adjusting a flight path of the aircraft 10 when the passenger's state is an emergency state or a second process for relieving tension when the passenger's state is a state of tension.

Specifically, in the first process according to an exemplary embodiment in the present disclosure, the control module 124 may control the communication module 129 to transmit an ID of the aircraft 10, a flight path of the aircraft 10, current location information of the aircraft 10, information of the passenger, biometric data of the passenger, and the captured image of the passenger to the control device 200 and to receive landing location information of a landing point of an adjacent hospital based on the current location information from the control device 200. Thereafter, the control module 124 may control the driving module 125 to land the aircraft 10 at the landing point by adjusting the flight path according to the received landing location information.

In addition, in the first process according to an exemplary embodiment in the present disclosure, the control module 124 may control the communication module 129 to receive a first aid process from the control device 200 and control the I/O module 121 to broadcast information on the emergency state, the first aid process, and a location of medical supplies.

Alternatively, in the first process according to an exemplary embodiment in the present disclosure, the control module 124 may control the driving module 125 to ascend or descend the altitude of the aircraft 10.

Meanwhile, in the second process according to an exemplary embodiment in the present disclosure, the control module 124 may control the I/O module 121 to provide music or images for relieving tension or control the convenience device 127 to induce a comfortable posture of the passenger.

The driving module 125 of the service providing apparatus 120 may be a module for driving the aircraft 10 so that the aircraft 10 may fly along a preset path or may land under the control of the control module 124 and may be, for example, a driving motor, a propeller, and the like.

The GPS module 126 of the service providing apparatus 120 is a module for receiving location information of the aircraft 10, and the received location information may be transmitted to the control module 124.

The convenience device 127 of the service providing apparatus 120 may include various devices, such as a variable bolster which may decrease or increase the volume of a pillow supporting the head so that the passenger's head is in a comfortable posture, footrests which may be adjusted in angle so that the passenger's legs are comfortable.

The storage module 128 of the service providing apparatus 120 may be a module for storing various programs for implementing functions performed by the control module 124 described above. In addition, the storage module 128 may store the ID of the aircraft 10, the flight path of the aircraft 10, the current location information of the aircraft 10, the information of the passenger, the biometric data of the passenger, the captured image of a passenger, the underlying disease of the passenger or disease according to family history, an estimated disease, and the like.

The communication module 129 of the service providing apparatus 120 may be a module for transmitting and receiving various types of data to and from the control device 200.

Meanwhile, the control device 200 may include a control module 210, a communication module 220, and a storage module 230.

Specifically, the control module 210 of the control device 200 may monitor a location of the aircraft 10 on the flight path. Also, when an emergency state is received from the service providing apparatus 120 of the aircraft 10, the control module 210 may transmit landing location information to the service providing apparatus 120 of the aircraft 10. The landing location information described above may be landing location information of a landing point of a nearby hospital based on the current location information of the aircraft 10. In addition, the emergency state may include the ID of the aircraft 10, the flight path of the aircraft 10, the current location information of the aircraft 10, the information of the passenger in an emergency state, the biometric data, the captured image, the underlying disease or the disease according to family history, the estimated disease, etc. The control module 210 of the control device 200 may further transmit a first aid process.

The communication module 220 of the control device 200 may be a module for transmitting and receiving various data to and from the service providing apparatus 120 of the aircraft 10.

The storage module 230 of the control device 200 may be a module for storing various programs for implementing functions performed by the control module 210.

In addition, the storage module 230 may store landing location information of a landing point of an adjacent hospital based on the current location information of the aircraft 10 and a first aid process for each disease.

In addition, the storage module 230 stores the ID of the aircraft 10, the flight path of the aircraft 10, the current location information of the aircraft 10, the information of the passenger in the emergency situation, the biometric data, the captured image, the underlying disease or the disease according to family history, and the estimated disease received from the service providing apparatus 120 of the aircraft 10.

As described above, according g to an exemplary embodiment in the present disclosure, the state of the passenger may be determined based on the biometric data and the captured image of a passenger, and an appropriate process may be performed according to the determined state of the passenger, thereby rapidly providing a service for the passenger in the state of tension or an emergency state.

Hereinafter, a method of providing a service according to a state of a passenger in an aircraft during an autonomous flight according to an exemplary embodiment in the present disclosure will be described with reference to FIGS. 3 to 5.

Figure 3:
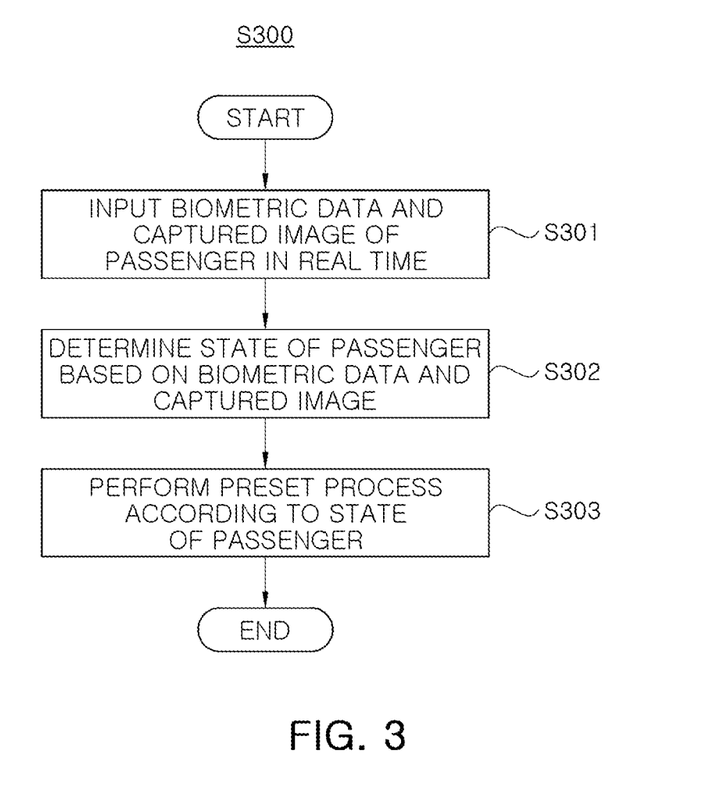
FIG. 3 is a flowchart illustrating a method of providing a service according to a state of a passenger in an aircraft during autonomous flight according to an exemplary embodiment in the present disclosure.

First, FIG. 3 is a flowchart illustrating a method of providing a service according to a state of a passenger in an aircraft during an autonomous flight according to an exemplary embodiment in the present disclosure. Also, FIG. 4 is a flowchart illustrating the first process performed in operation S303 of FIG. 3, and FIG. 5 is a flowchart illustrating the second process performed in operation S303 of FIG. 3.

First, as illustrated in FIG. 3, the method (S300) of providing a service according to a state of a passenger in an aircraft during an autonomous flight according to an exemplary embodiment in the present disclosure may start as the I/O module 121 receives biometric data and a captured image of a passenger in real time (S301). The input biometric data and captured image of the passenger may be transmitted to the determination module 122.

The biometric data of the passenger may include at least one of a heart rate, a sweat output, a grip strength, a blood pressure, a body temperature, and a respiration rate of the passenger. Such biometric data may be measured through the sensor module 111, the captured image may be captured through the camera 112 as described above.

Next, the determination module 122 may determine a state of the passenger based on the biometric data and the captured image (S302). Here, the state of the passenger may be an emergency state or a state of tension.

Specifically, when the determination module 122 may determine whether a state of the passenger is an emergency state based on a combination of classification result from the machine learning model 123 to which the captured image of a passenger is input and comparison result between at least one of a heart rate, a sweat output, a grip strength, a blood pressure, and a respiration rate of the passenger with each preset reference value. The aforementioned reference value may vary depending on the gender, age, etc. of the passenger, but is not limited to a specific value here.

In addition, the machine learning model 123 described above may include a first machine learning model 123a for classifying a facial expression of the passenger in the captured image and a second machine learning model 123b for classifying a body posture of the passenger in the captured image.

Specifically, the first machine learning model 123a may classify the facial expression of the passenger as pain, fear, tension, disgust, stuffiness, discomfort, and others. Here, the others may include facial expressions other than pain, fear, tension, disgust, stuffiness, and discomfort.

In addition, the second machine learning model 123b may classify the body posture of the passenger as one of a posture with eyes closed, a posture with hands put on the head, a posture in which the face is lowered down forwardly and is not visible, and others. Here, the others may be body postures other than the posture with eyes closed, the posture with hands put on the head, and the posture in which the face is lowered down forwardly and is not visible.

As described above, the type and classification result of biometric data used when determining such an emergency state may be different for each disease.

Therefore, according to an exemplary embodiment in the present disclosure, whether the state of the passenger is an emergency state maybe be determined based on a combination of classification result from the machine learning model 123 to which the captured image of a passenger is input and comparison result between at least one of a heart rate, a sweat output, a grip strength, a blood pressure, and a respiration rate of the passenger with each preset reference value.

In addition, based on the combination of classification results from the machine learning model 123 to which the captured image is input and the comparison result between at least one of the heart rate, sweat output, grip strength, blood pressure, and respiration rate of the passenger with each preset reference value, the determination module 122 may further estimate a disease. However, when there are multiple estimated diseases, the determination module 122 may estimate a disease by considering a disease according to the underlying disease of the passenger or family history as a priority.

In addition, based on the classification result from the first machine learning model 123a to which the captured image is input or the comparison result between at least one of the heart rate, sweat output, grip strength, blood pressure, and respiration rate of the passenger with each preset reference value, the determination module 122 may determine whether the passenger is in a state of tension and the classification result from the first machine learning model 123a may be tension.

According to an exemplary embodiment in the present disclosure, based on the classification result from the first machine learning model 123a to which the captured image is input and the comparison result between at least one of the heart rate, sweat output, grip strength, blood pressure, and respiration rate of the passenger with each preset reference value, the determination module 122 may determine whether the passenger is in a state of tension.

Referring back to FIG. 3, the control module 124 may perform a preset process according to the state of the passenger (S303). Here, the preset process may include a first process for adjusting a flight path of the aircraft 10 when the passenger's state is an emergency state or a second process for relieving tension when the passenger's state is a state of tension, as described above.

Figure 4:
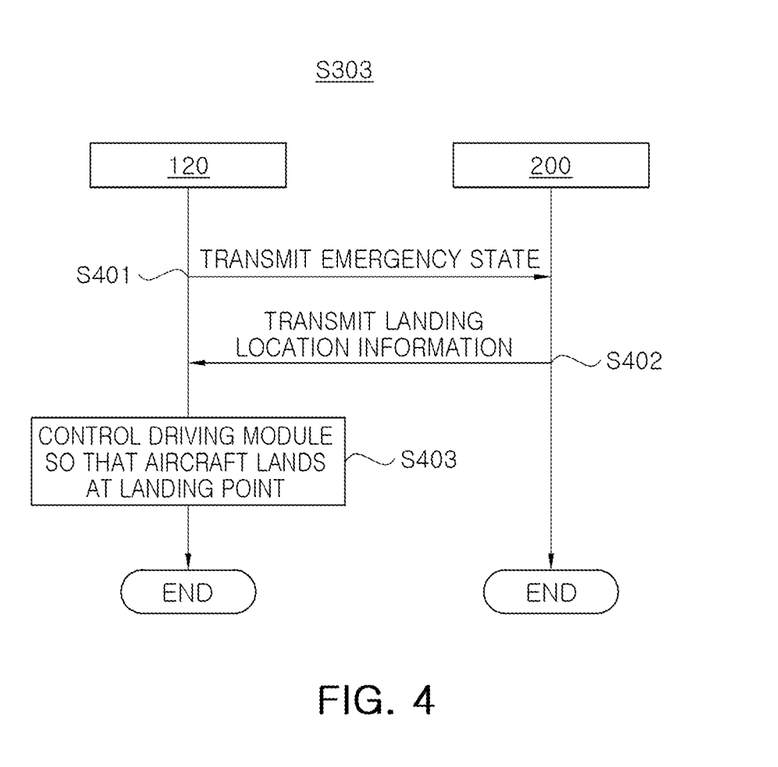
FIG. 4 is a flowchart illustrating a first process performed in operation S303 of FIG. 3.

FIG. 4 is a flowchart illustrating the first process performed in operation S303 of FIG. 3.

Referring to FIG. 4, the service providing apparatus 120 may transmit an emergency state to the control device 200 (S401). The emergency state described above may include the ID of the aircraft 10, the flight path of the aircraft 10, the current location information of the aircraft 10, the information of the passenger in an emergency state, the biometric data, the captured image, the underlying disease or the disease according to family history, the estimated disease, etc. as described above.

Thereafter, the control device 200 may transmit landing location information to the service providing apparatus 120. As described above, a first aid process may be further transmitted according to an exemplary embodiment of the present disclosure.

Thereafter, the service providing apparatus 120 may control the driving module 125 to land the aircraft at the landing point by adjusting the flight path according to the received landing location information (S403).

Meanwhile, according to the first process according to an exemplary embodiment in the present disclosure, the service providing apparatus 120 may control the communication module 129 to receive a first aid process from the control device 200, and may control the input/output module 121 to broadcast information on the emergency state, the first aid process, and a location of medical supplies, as described above.

Alternatively, according to the first process according to an exemplary embodiment present disclosure, the service providing apparatus 120 may control the driving module 125 to ascend or descend the altitude of the aircraft 10 as described above.

Figure 5:
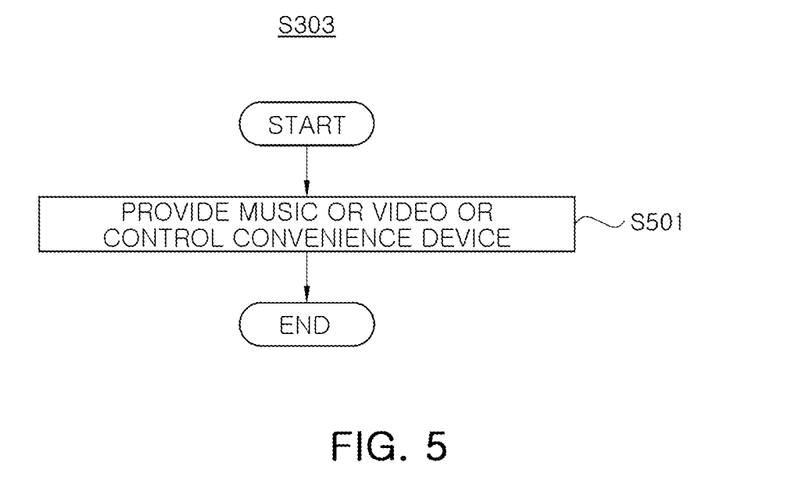
FIG. 5 is a flowchart illustrating a second process performed in operation S303 of FIG. 3.

Meanwhile, FIG. 5 is a flowchart illustrating the second process performed in operation S303 of FIG. 3.

As illustrated in FIG. 5, according to the second process according to an exemplary embodiment in the present disclosure, the service providing apparatus 120 may control the I/O module 121 to provide music or images for relieving tension or control the convenience device 127 to induce a comfortable posture of the passenger (S501).

As described above, according to an exemplary embodiment in the present disclosure, a state of a passenger may be determined based on biometric data and a captured image of the passenger, and an appropriate process may be performed according to the determined state of the passenger, thereby quickly providing a service for the passenger's tension or emergency state.

Figure 6:
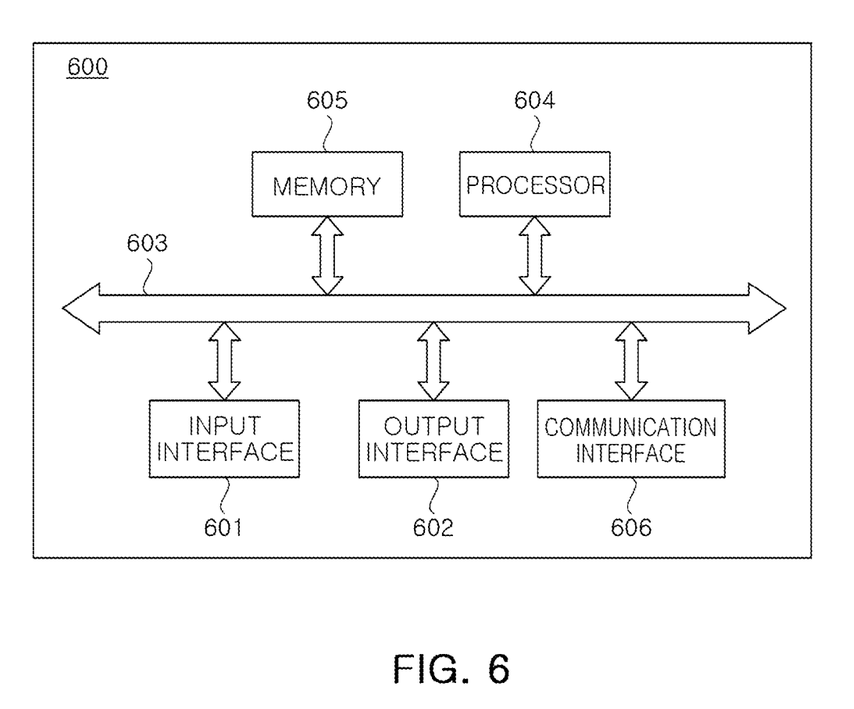
FIG. 6 is a block diagram of a computer device which may fully or partially implement a service providing apparatus or a control device according to an exemplary embodiment in the present disclosure.

Meanwhile, FIG. 6 is a block diagram of a computer device which may fully or partially implement a service providing apparatus or a control device according to an exemplary embodiment in the present disclosure, and may be applied to the service providing apparatus 120 and the control device 200 illustrated in FIG. 2.

As illustrated in FIG. 6, a computer device 600 may include an input interface 601, an output interface 602, a processor 604, a memory 605, and a communication interface 606, and the input interface 601, the output interface 602, the processor 604, the memory 605, and the communication interface 606 may be interconnected through a system bus 603.

In an exemplary embodiment of the disclosure, the memory 605 may be used to store programs, instructions, or codes, and the processor 604 may execute the programs, instructions, or codes stored in the memory 605, may receive a signal by controlling the input interface 601, and may transmit a signal by controlling the output interface 602. The aforementioned memory 605 may include read-only memory and random access memory, and may provide instructions and data to the processor 604.

In an exemplary embodiment in the present disclosure, the processor 604 may be a central processing unit (CPU) and may be understood as being another general-purpose processor, a digital signal processor (DSP), an application specific integrated circuit (ASIC), a field programmable gate array (FPGA) or other programmable logic devices, discrete gate or transistor logic device, discrete hardware component, etc. The general-purpose processor may be a microprocessor, or the corresponding processor may be any conventional processor or the like.

In an implementation process, the method performed in each device of FIG. 2 may be achieved by an integrated logic circuit of hardware in the processor 604 or an instruction in the form of software. Contents of a method disclosed in relation to an exemplary embodiment in the present disclosure may be implemented to be performed and completed by a hardware processor or may be implemented to be performed and completed by a combination of hardware and software modules of a processor. The software module may be disposed in a storage medium, such as random access memory, flash memory, read-only memory, programmable read-only memory or electrically erasable programmable memory, registers, or the like. The corresponding storage medium is located in the memory 605, and the processor 604 reads the information of the memory 605, and implements the contents of the above method in combination with hardware. To avoid redundancy, detailed descriptions are omitted here.

Meanwhile, in the present disclosure, '~ module' may be implemented in various manners, for example, a processor, program instructions executed by the processor, software modules, microcodes, computer program products, logic circuits, application-specific integrated circuits, firmware, etc.

While exemplary embodiments have been illustrated and described above, it will be apparent to those skilled in the art that modifications and variations could be made without departing from the scope of the present disclosure as defined by the appended claims.

What is claimed is:

1. A service providing apparatus of providing a service according to a state of a passenger in aircraft during autonomous flight, the apparatus comprising:
   a processor; and
   a storage medium recording one or more programs configured to be executable by the processor,
      wherein the one or more programs include instructions for:
      an input/output (I/O) module receiving biometric data and a captured image of the passenger in real time;
      a determination module determining the state of the passenger based on the biometric data and the captured image of the passenger; and
      a control module performing a preset process according to the state of the passenger,
      wherein the preset process includes:
      a first process for adjusting a flight path of the aircraft when the state of the passenger is an emergency state or a second process for relieving tension when the state of the passenger is a state of tension,
      wherein the biometric data includes at least one of a heart rate, a sweat output, a grip strength, a blood pressure, a body temperature, and a respiration rate of the passenger, and
      wherein the determination module determines whether the state of the passenger is the emergency state based on a combination of classification result from the machine learning model to which the captured image of the passenger is input and comparison result between at least one of the heart rate, the sweat output, the grip strength, the blood pressure, and the respiration rate of the passenger with each preset reference value, and
      a type of biometric data and a classification result used in determining the emergency state are different for each disease.

2. The service providing apparatus of claim 1, wherein the machine learning model includes:
   a first machine learning model for classifying a facial expression of the passenger in the captured image of the passenger; and a second machine learning model for classifying a body posture of the passenger in the captured image of the passenger.

3. The service providing apparatus of claim 2, wherein the first machine learning model classifies the facial expression of the passenger as pain, fear, tension, disgust, stuffiness, discomfort, and others.

4. The service providing apparatus of claim 2, wherein the second machine learning model classifies the body posture of the passenger as one of a posture with eyes closed, a posture with hands put on the head, a posture in which a face is lowered down forwardly and is not visible, and others.

5. The service providing apparatus of claim 1, wherein
the determination module estimates the disease based on the combination of classification result from the machine learning model to which the captured image of the passenger is input and comparison result between at least one of the heart rate, the sweat output, the grip strength, the blood pressure, and the respiration rate of the passenger with each preset reference value, and
when there are multiple estimated diseases, the determination module considers a disease according to an underlying disease of the passenger or family history as a priority among the multiple estimated diseases.

6. The service providing apparatus of claim 2, wherein
the determination module determines whether the state of the passenger is a state of tension based on a classification result from the machine learning model to which the captured image of the passenger is input or comparison result between at least one of the heart rate, the sweat output, the grip strength, the blood pressure, and the respiration rate of the passenger with each preset reference value, and
the classification result from the first machine learning model is tension.

7. The service providing apparatus of claim 1, wherein
the first process is a process of controlling a communication module to transmit an ID of the aircraft, a flight path of the aircraft, current location information of the aircraft, information of the passenger, biometric data of the passenger, and the captured image of the passenger to a control device and to receive landing location information of a landing point of an adjacent hospital based on the current location information from the control device, and
controlling a driving module to land the aircraft at the landing point by adjusting the flight path according to the received landing location information.

8. The service providing apparatus of claim 1, wherein
the first process is a process of controlling a communication module to receive a first aid process from a control device, and
controlling the I/O module to broadcast information on the emergency state, the first aid process, and a location of medical supplies.

9. The service providing apparatus of claim 1, wherein the first process further includes a process of controlling a driving module to ascend or descend an altitude of the aircraft.

10. The service providing apparatus of claim 1, wherein
the second process includes a process of controlling the I/O module to provide music or video for relieving the tension and
a process of controlling a convenience device for inducing a comfortable posture of the passenger.

11. A method of providing a service according to a state of a passenger in aircraft during autonomous flight, the method comprising:
a first operation in which an input/output (I/O) module receives biometric data and a captured image of the passenger in real time;
a second operation in which a determination module determines the state of the passenger based on the biometric data and the captured image of the passenger; and
a third operation in which a control module performs a preset process according to the state of the passenger,
wherein the preset process includes:
a first process for adjusting a flight path of the aircraft when the state of the passenger is an emergency state or a second process for relieving tension when the state of the passenger is a state of tension,
wherein the biometric data includes at least one of a heart rate, a sweat output, a grip strength, a blood pressure, a body temperature, and a respiration rate of the passenger, and
in the second operation,
determining whether the state of the passenger is an emergency state based on a combination of classification result from the machine learning model to which the captured image of the passenger is input and comparison result between at least one of the heart rate, the sweat output, the grip strength, the blood pressure, and the respiration rate of the passenger with each preset reference value, and
a type of biometric data and a classification result used in determining the emergency state are different for each disease.

12. The method of claim 11, wherein
the machine learning model includes:
a first machine learning model for classifying a facial expression of the passenger in the captured image of the passenger; and
a second machine learning model for classifying a body posture of the passenger in the captured image of the passenger.

13. The method of claim 12, wherein the first machine learning model classifies the facial expression of the passenger as pain, fear, tension, disgust, stuffiness, discomfort, and others.

14. The method of claim 12, wherein the second machine learning model classifies the body posture of the passenger as one of a posture with eyes closed, a posture with hands put on the head, a posture in which a face is lowered down forwardly and is not visible, and others.

15. The method of claim 11, wherein the second operation further includes estimating the disease based on a combination of classification result from the machine learning model to which the captured image of the passenger is input and comparison result between at least one of the heart rate, the sweat output, the grip strength, the blood pressure, and the respiration rate of the passenger with each preset reference value and when there are multiple estimated diseases, considering a disease according to an underlying disease of the passenger or family history as a priority among the multiple estimated diseases.

16. The method of claim 12, wherein,
in the second operation,
determining whether the state of the passenger is a state of tension based on classification result from the machine learning model to which the captured image of the passenger is input or comparison result between at least one of the heart rate, the sweat output, the grip strength, the blood pressure, and the respiration rate of the passenger with each preset reference value, and the classification result from the first machine learning model is tension.

* * * * *